US012582771B2

(12) United States Patent
Abal et al.

(10) Patent No.: US 12,582,771 B2
(45) Date of Patent: Mar. 24, 2026

(54) INTEGRATED LIQUID FLOW CLOSED LOOP SENSING AND CONTROL

(71) Applicant: CareFusion 303, Inc., San Diego, CA (US)

(72) Inventors: Daniel M. Abal, San Diego, CA (US); Brendan John Burgess, Poway, CA (US); Ramkumar Subramanian, San Diego, CA (US); Jay Jyotindra Dave, Carlsbad, CA (US)

(73) Assignee: CAREFUSION 303, INC., San Diego, CA (US)

( * ) Notice: Subject to any disclaimer, the term of this patent is extended or adjusted under 35 U.S.C. 154(b) by 7 days.

(21) Appl. No.: 18/397,882

(22) Filed: Dec. 27, 2023

(65) Prior Publication Data

US 2024/0123146 A1 Apr. 18, 2024

Related U.S. Application Data

(63) Continuation of application No. 17/326,210, filed on May 20, 2021, now Pat. No. 11,857,762.
(Continued)

(51) Int. Cl.
| | |
|---|---|
| *A61M 5/172* | (2006.01) |
| *H01R 13/15* | (2006.01) |
| *H02J 50/10* | (2016.01) |

(52) U.S. Cl.
CPC ..... *A61M 5/172* (2013.01); *A61M 2205/3334* (2013.01); *A61M 2205/3584* (2013.01);
(Continued)

(58) Field of Classification Search
CPC ................ A61M 5/1413; A61M 5/142; A61M 5/16804; G16H 20/17
See application file for complete search history.

(56) References Cited

U.S. PATENT DOCUMENTS

| | | | |
|---|---|---|---|
| 5,453,098 A | 9/1995 | Botts et al. | |
| 5,713,856 A * | 2/1998 | Eggers | G16H 70/40 |
| | | | 604/65 |

(Continued)

FOREIGN PATENT DOCUMENTS

| | | |
|---|---|---|
| CN | 101405043 A | 4/2009 |
| CN | 110099708 A | 8/2019 |

(Continued)

OTHER PUBLICATIONS

Japanese Office Action for Application No. 2022-572574, dated Sep. 3, 2024, 4 pages including translation.
(Continued)

*Primary Examiner* — Laura A Bouchelle
(74) *Attorney, Agent, or Firm* — MASCHOFF BRENNAN

(57) ABSTRACT

An integrated intravenous (IV) administration set includes a flow stop having a tubing fitment and a housing, the flow stop configured, in a first position, to prevent a flow of a fluid through the tubing, and in a second position, to permit the flow of the fluid through the tubing, the tubing fitment comprising a protrusion configured to receive a tubing. The IV administration set also includes an electronic flow sensor disposed within the housing, the electronic flow sensor configured to measure a flow of a fluid in the tubing, and one or more conductive connections configured within the housing and configured to provide electrical power to the electronic flow sensor. The flow stop is shaped to be loaded and engaged to a receptacle of an infusion device, and shaped to cause, when loaded and engaged, the one or more conductive connections to engage with a corresponding conductive connection provided by the infusion device to activate the flow sensor based on a power flow from the infusion device.

16 Claims, 9 Drawing Sheets

Related U.S. Application Data

(60) Provisional application No. 63/030,234, filed on May 26, 2020.

(52) U.S. Cl.
CPC ......... *A61M 2205/52* (2013.01); *H01R 13/15* (2013.01); *H01R 2201/12* (2013.01); *H01R 2201/20* (2013.01); *H02J 50/10* (2016.02)

(56) References Cited

U.S. PATENT DOCUMENTS

| | | | |
|---|---|---|---|
| 7,124,996 | B2 | 10/2006 | Clarke et al. |
| 11,324,888 | B2 | 5/2022 | Shubinsky |
| 2010/0280486 | A1 | 11/2010 | Khair et al. |
| 2013/0204227 | A1 | 8/2013 | Bochenko et al. |
| 2019/0262535 | A1 | 8/2019 | Shubinsky et al. |

FOREIGN PATENT DOCUMENTS

| | | | | | |
|---|---|---|---|---|---|
| EP | 1951362 | A1 | 8/2008 | | |
| EP | 3278823 | A1 | 2/2018 | | |
| JP | H08080348 | A | 3/1996 | | |
| JP | 2009515601 | A | 4/2009 | | |
| JP | 2012525207 | A | 10/2012 | | |
| WO | WO-2015073604 | A1 | * 5/2015 | ............ | A61M 5/365 |

OTHER PUBLICATIONS

International Search Report and Written Opinion for Application No. PCT/US2021/034340, dated Nov. 12, 2021, 16 pages.
Invitation to Pay Additional Fees for Application No. PCT/US2021/034340, dated Sep. 13, 2021, 14 pages.
Chinese Office Action for Application No. 202180041786.X, dated May 20, 2025, 11 pages including translation.
Extended European Search Report for Application No. 25202385.8, dated Nov. 3, 2025, 9 pages.

* cited by examiner

1

INTEGRATED LIQUID FLOW CLOSED LOOP SENSING AND CONTROL

CROSS REFERENCE TO RELATED APPLICATIONS

This application is a continuation of U.S. patent application Ser. No. 17/326,210, filed on May 20, 2021, issued as U.S. Pat. No. 11,857,762 on Jan. 2, 2024, which claims the benefit of U.S. Provisional Application No. 63/030,234, filed on May 26, 2020, the entirety of each of which is incorporated herein by reference for all purposes.

TECHNICAL FIELD

This application relates generally to sensing and controlling liquid flows in infusion processes.

BACKGROUND

Infusion pumps generally monitor a flow rate of a fluid that is dispensed. There is a desire to improve efficiency, sensitivity, and accuracy of infusion pumps to sense and control liquid flows having a large range of dynamic flow rates during infusion processes.

SUMMARY

Over-infusion of a therapeutic fluid occurs when there are variations between a target flow rate set at an infusion device and an actual flow rate of the therapeutic fluid through an intravenous (IV) administration set and infused to a patient.

Accordingly, there is a desire to improve efficiency, sensitivity, and accuracy of detection of over-infusion or under-infusion. IV administration sets are typically single-use disposable consumables for infusion processes. Thus, they generally do not contain sensors or other electronics that monitor or control fluid flows. IV set described herein include liquid sensing capabilities and closed loop flow control circuitry, and are coupled to a mechanical flow stop, forming an integrated platform for flow control and sensing. In some implementations, a flow stop may be referred to as a flow clamp, a safety clamp, or a slide clamp. The devices and methods described herein provide closed loop flow control for infusion pumps that monitor an actual flow rate and adjust the pump or alert the user when there is any deviation from a set flow rate under normal operation or fault conditions.

The disclosed subject matter relates to an integrated intravenous (IV) administration set that includes a tubing fitment, the tubing fitment includes a protrusion configured to receive a tubing of the IV administration set. The set includes a housing coupled to the tubing fitment; an electronic flow sensor disposed within the housing, the electronic flow sensor configured to measure a flow of a fluid in the tubing. The set includes one or more conductive connections configured to provide electrical power to the electronic flow sensor and to transmit data; and a flow stop configured, in a first position, to prevent a flow of a fluid through the tubing, and in a second position, to permit the flow of the fluid through the tubing. The tubing fitment is shaped to be loaded and engaged to an infusion device configured with a corresponding receptacle for maintaining an alignment of the housing with respect to the infusion device.

The integrated IV administration set includes control circuitry for closed loop flow control of the flow of the fluid, the closed loop flow control based on data measured by the electronic flow sensor. The control circuitry is configured to send a control signal to the infusion device to modify a flow rate generated by a pumping mechanism of the infusion device.

In another aspect, a sensor system includes a first plurality of conductive connections; a data port to receive data recorded by an electronic flow sensor of an integrated intravenous (IV) administration set, wherein the integrated IV administration set includes a second plurality of conductive connections configured to interface with the first plurality of conductive connections when the integrated IV administration set engages with the sensor system; and the sensor system is configured to provide control signals to an infusion device based on the data recorded by the electronic flow sensor to maintain a fluid flowing through the integrated IV administration set at a desired flow rate.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

There is a desire to monitor the fluid flow in infusion processes more accurately. Unregulated flow, such as over-infusion and under-infusion, of a therapeutic fluid occurs when there are variations between a target flow rate set at an infusion device and an actual flow rate of the therapeutic fluid through an IV administration set and infused to a patient.

The devices and methods described herein provide an integrated IV administration set that incorporates electronic sensing and control of fluid flows.

Figure 1:
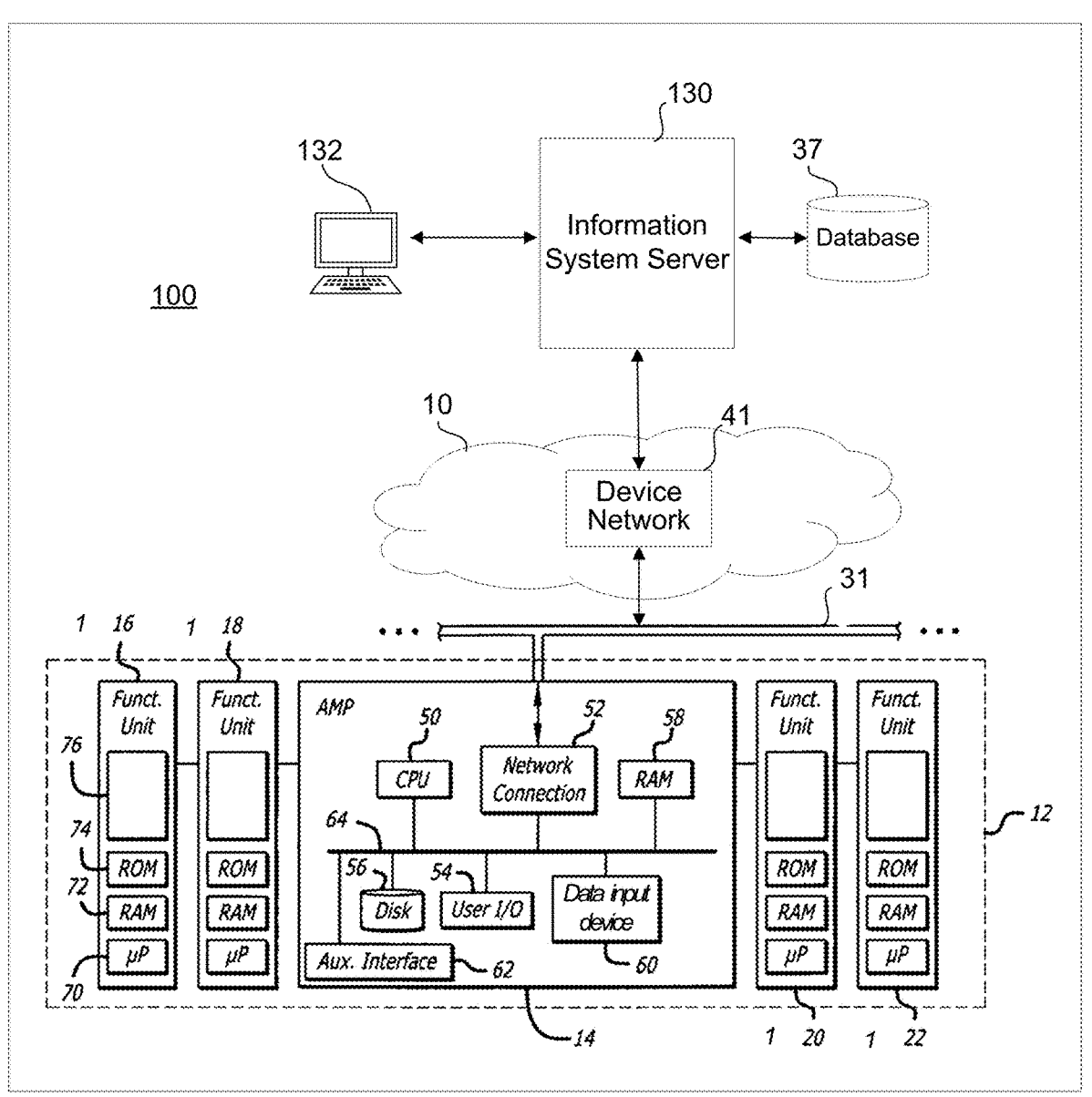
FIG. 1 depicts an example of an institutional patient care system of a healthcare organization, according to aspects of the subject technology.

FIG. 1 depicts an example of an institutional patient care system 100 of a healthcare organization, according to aspects of the subject technology. In FIG. 1, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 41 by which patient care devices 12 (and other devices) communicate in accordance with normal operations.

Additionally, institutional patient care system 100 may incorporate a separate information system server 130, the function of which will be described in more detail below. Moreover, although the information system server 130 is shown as a separate server, the functions and programming of the information system server 130 may be incorporated into another computer, if such is desired by engineers designing the institution's information system. Institutional patient care system 100 may further include one or multiple device terminals 132 for connecting and communicating with information system server 130. Device terminals 132 may include personal computers, personal data assistances, mobile devices such as laptops, tablet computers, augmented reality devices, or smartphones, configured with software for communications with information system server 130 via network 10.

Patient care device 12 comprises a system for providing patient care, such as that described in Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 116, 118, 120, 122. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system or located externally and communicating with pharmacy system through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20, 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1C, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. The configuration database may be a database 56 internal to patient care device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 52 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figure 2:
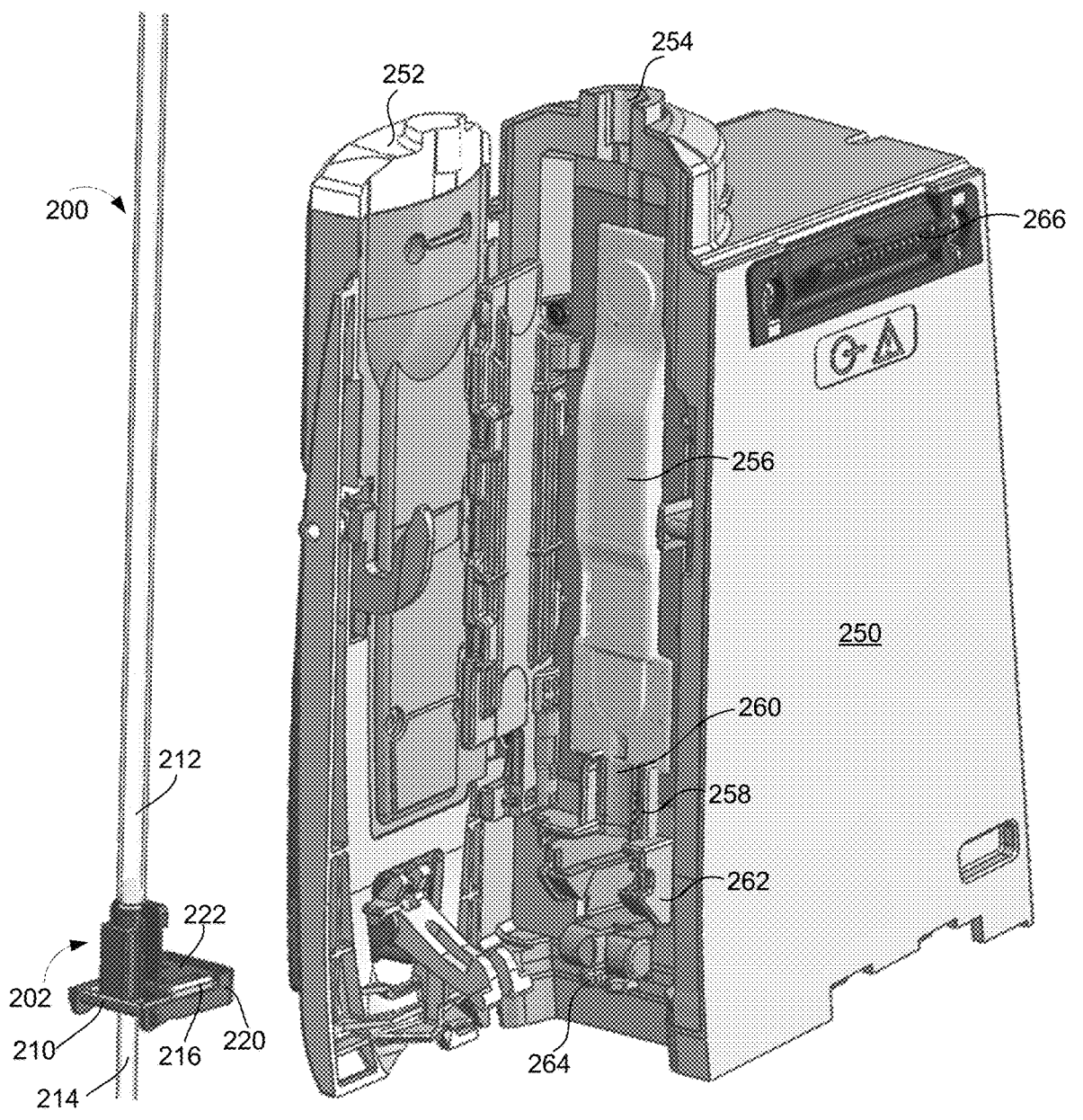
FIG. 2 depicts an example of an integrated administration set and an infusion pump, according to aspects of the subject technology.
Figures 4A, 4B, 4C:
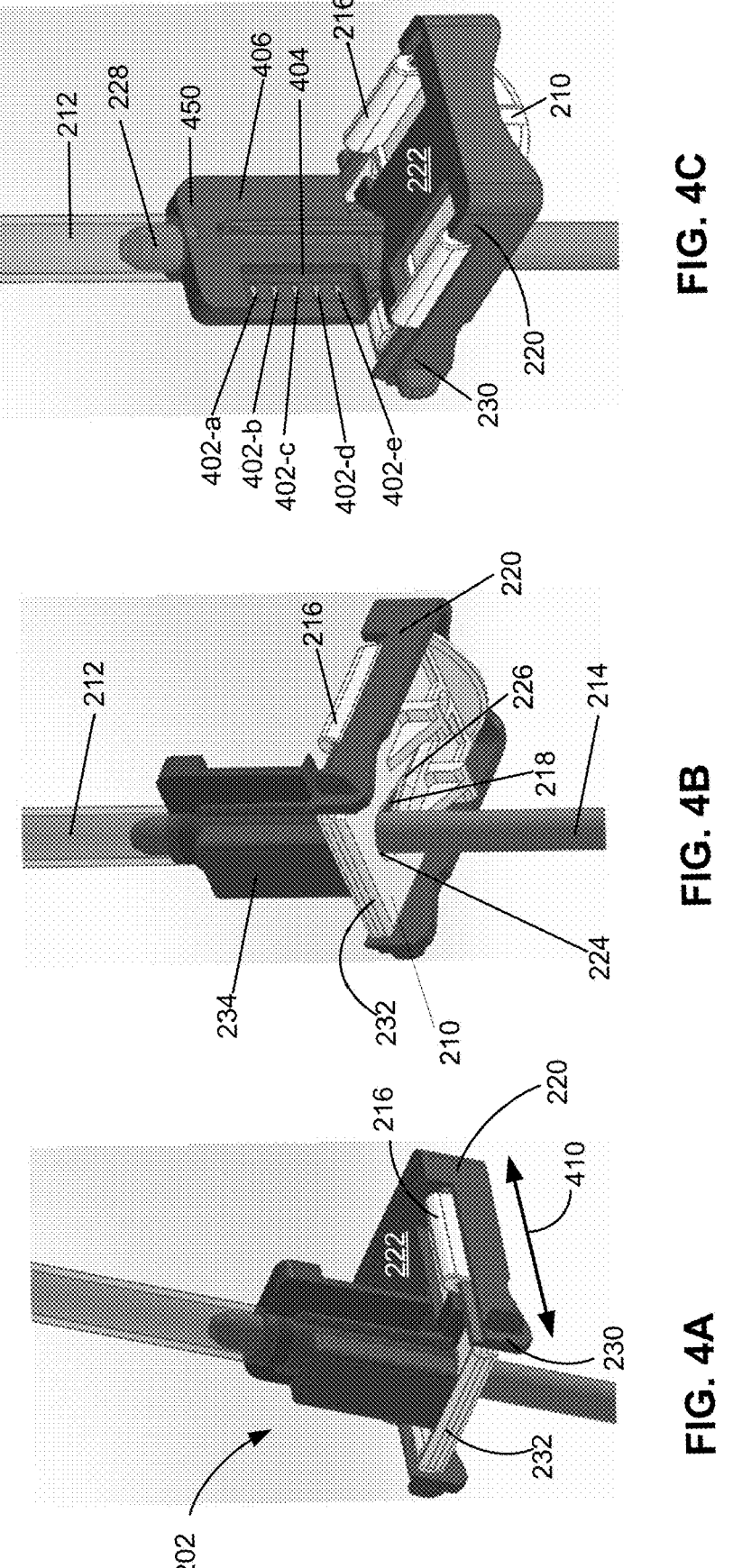
FIG. 4A depicts a first perspective view of an integrated flow stop system, according to aspects of the subject technology.
FIG. 4B depicts a second perspective view of an integrated flow stop system, according to aspects of the subject technology.
FIG. 4C depicts a third perspective view of an integrated flow stop system, according to aspects of the subject technology.

FIG. 2 depicts an example an integrated administration set and an infusion pump, according to aspects of the subject technology. In some implementations, an administration set 200 includes an integrated flow stop system 202. The integrated flow stop system 202 provides closed loop control and flow sensing, in addition to functioning as a mechanical flow stop device. FIGS. 4A-4C provide different views of the integrated flow stop system 202. IV administration sets are typically single-use disposable consumables. Thus, they generally do not contain sensors or other electronics that monitor or control fluid flows. In contrast, the integrated IV set 200 includes liquid sensing capabilities and closed loop flow control circuitry, enhancing the accuracy and efficiency for sensing of the flow rate directly at the administration set and improving overall control of flow rates based, at least in part, on the sensed values.

A closed loop control system (or feedback control system) can automatically regulate a process variable to a desired set point with limited or, in some cases, no human interaction. The control circuitry in the integrated flow stop system 202 detects the flow rate of the infusion process by generating control messages to adjust one or more elements of a patient care device. A control message may be generated based on a set (e.g., desired) flow rate provided at an infusion pump in comparison to a detected flow rate for the infusion pump. A closed loop control system includes one or more feedback loops between its output values and its input values. A closed-loop control system can generate an error signal that reflects a difference between its output values (e.g., the flow rate measured by the flow sensor) and its reference input value (e.g., the set flow rate provided at the infusion pump), and the control message generated by the closed-loop control system is dependent on the output value. For example, the control signal sent by the control circuitry changes an operational parameter of the infusion pump in order to bring the measured flow rate as close as possible to the set (e.g. desired) flow rate.

FIG. 2 depicts the administration set 200 coupled to a large volume pump (LVP) 250. In some implementations, the administration set 200 is used with syringe pumps or other infusion pump systems. The LVP 250 includes a door 252, an upper tubing fitment receptacle 254, and a pumping mechanism 256. The LVP 250 also includes a molded feature 260 having a shape complementary to a corresponding portion of the integrated flow stop system 202. In this way, the molded feature 260 ensures a snug fit of the integrated flow stop system 202 when the IV administration set 200 is loaded into and engaged with the pump 250.

A first plurality of conductive connections 258 on the pump 250 (FIG. 2 depicts 4 different conductive connections) permits electricity and data to flow between the pump 250 and the integrated flow stop system 202 when the integrated IV administration set 200 is loaded into, and engaged with the pump 250. Each of the conductive connections 258 may be formed of the same material or different material depending on the conductive path formed. For example, a conductive connection for power may be formed from a metal or other material for conducting electricity while a data connection may be formed from a metallic or fiber optic conductive material to form a data pathway. The pump 250 also includes a retainer 264 to secure the tubing 214. The pump 250 includes an inter-unit interface (IUI) connector 266. The IUI connector 266 establishes power and communications between the pump 250 and various attached modules.

A receiving portion 262 in the pump 250 defines a slot into which a tubing fitment 222 of the integrated flow stop system 202 is loaded. The flow stop 210 is coupled to and positioned below the tubing fitment 222. As explained in more details in reference to FIGS. 4A-4C, the flow stop 210 is configured to slide between two positions.

In a first position (the open position), the flow stop 210 lines up with the tubing fitment 222 (as shown in FIG. 4B), and a flow of a fluid in the tubing 214 is not occluded. In a second position (the closed position), the flow stop 210 slides toward the tubing 214, protruding from under the tubing fitment 222, and mechanically clamps the tubing 214 to occlude the flow of the fluid.

In some implementations, the flow stop 210 is in the open position when the administration set 200 is loaded into the pump 250. During an infusion process, the door 252 is closed and the flow stop 210 stays in the open position to permit fluid flow. When the door 252 opens (e.g., accidentally) during the infusion process, the flow stop 210 automatically changes to the closed position, mechanically pinching the tubing 214 to prevent accidental discharge of the fluid.

The integrated flow stop system 202 adds electronically controlled functionalities to the flow stop. In some implementations, upon loading the integrated administration set 200 into the pump 250, the flow stop 210 is engaged (e.g., remains in the open position) and the plurality of conductive connections 258 interfaces to the corresponding conductive connections on the integrated flow stop system 202. The conductive connections provide electrical power to an electronic flow sensor 406 (shown in FIG. 4C) disposed within a housing 450 of the integrated flow stop system 202, activating the electronic flow sensor 406. In addition to conducting electricity, the plurality of conductive connections 258 also permits sensor data and/or control signals from the flow sensor 406 or closed loop control circuitry to be relayed to the pump 250.

For example, in some implementations, the control signals from the closed loop control circuitry change an operational parameter of the pumping mechanism 256 to cause a measured flow rate at the electronic flow sensor 406 to shift closer in value to the desired set flow rate programmed at the pump 250.

In some implementations, the integrated flow stop system 202 also includes non-volatile memory components configured to store identification information of the administration set 200. For example, upon correct loading and engagement of the integrated flow stop system 202 into the pump 250, data stored in the non-volatile memory component is read by the pump 250. In some implementations, the memory components store information about how long the administration set 200 has been in use. For example, a circuitry (e.g., an electronic time counter) disposed in the integrated flow stop system 202 records the length of time over which the integrated flow stop system 202 receives electricity from the plurality of conductive connections 258. In some implementations, the memory components also store flow rate data measured by the electronic flow sensor 406.

In some implementations, the integrated flow stop system 202 includes a wireless communication module. The flow rate data measured by the electronic flow sensor 406 is uploaded directly to a server system (e.g., of a hospital system) that monitors the operation of the pump 250. In some implementations, the pump 250 stores flow rates values for different infusion fluid types, and modifies its operational parameters based on flow rates measured by the electronic flow sensor 406. The pump 250 receives the measured flow rates relayed directly by the integrated flow stop system 202 or transmitted from the server system.

In some implementations, the identification information stored on the non-volatile memory includes a manufacture date of the administration set, allowing the pump 250 to determine a shelf-life of the administration set that is being loaded into the pump 250. Once conductive connections (e.g., through the plurality of conductive connections 258) are established between the integrated flow stop system 202 and the pump 250, the pump 250 can obtain shelf-life information from the administration set 200. The shelf-life information may identify an expiration date for the set after which the set should not be used. To ensure patient safety, the pump 250 can block infusion processes on an administration set that has exceeded the identified shelf-life. The identification information may include additional or alternative information regarding the use of the administration set 200. For example, the identification information may include a maximum time of use for the administration set 200. In such instances, the pump 250 can terminate an infusion process and/or sound an alarm when the administration set 200 has been in use for longer than the maximum time of use. This can help to minimize infection risks associated with over-extended use of the administration set. Other use information may include drug type(s) that can or cannot be infused with the administration set, pumps or pump modules that are compatible with the administration sets, or calibration values that can be used to improve an accuracy of the pressure sensing and an accuracy of flow delivery performance. In some implementations, additional information can be provided via the flow stop system 202, such as whether the IV bag is empty and has no flow, whether there is an occlusion condition due to pressure building up and affecting the flow pattern. If the sear on the flow stop does not engage or engages in a manner that is not within specifications, unregulated flow can result. The flow stop systems described herein may be able to detect such conditions because the pump module is able to communicate with the flow stop.

Incorporating electronic functionalities into the integrated flow stop system 202 allows easy association of the flow sensor (in a particular administration set) to the pump. For a pump having multi-channel infusion capabilities, automatically establishing a data channel between the pump and the flow sensor of each administration set (e.g., through the plurality of conductive connections 258) minimizes errors (e.g., of associating the wrong flow rate with the wrong infusion channel) and reduces the need for manual checks of the administration set during loading or during an infusion process from a health care professional. In some implementations, the IV bag and set are prepared together by the pharmacy. An identification ("ID") number can be associated with both the IV bag and the administration set. The ID number can be read by the pump and correlated to the medication, the flow rate, and volume to be administered to the patient. The pump can be programed based on these parameters without the need for a clinician to enter these values. In some implementations, such information can be provided by the integrated flow stop system 202.

In some implementations, the plurality of conductive connections 258 includes spring loaded pogo pin type connectors. In some implementations, conductive connections 258 are made from an elastomeric plastic conductor material. In some implementations, there is contactless transfer of power and/or data between the integrated flow stop system 202 and the pump 250. The contactless transfer of power includes inductive coupling elements. For example, the pump 250 includes a transmitter device, driven by electric power from a power source to generate a time-varying electromagnetic field. The electromagnetic field transmits power across space to a receiver device in the integrated flow stop system 202. The receiver device extracts power from the electromagnetic field and supplies it to an electrical load (e.g., the electronic flow sensor 406 and/or the control circuitry).

The molded feature 260 in the housing of the pump 250 receives, centers, and locates the housing 450 (and the components such as the electronic flow sensor 406) of the integrated flow stop system 202, and ensures alignment of the flow stop 210, and electrical contacts between the integrated flow stop system 202 and the pump 250.

At slow flow rates, the pump can create large relative changes in the flow rate even with minor deviations (e.g., a minor change in the flow rate constitutes a large percentage change when the flow rate is small). In other words, a small (absolute) changes in the flow rate results in a large percentage (e.g., relative) change. The large relative changes limit a dynamic range of flow rates that a flow sensor can reliably detect.

In addition, regions close to the pumping mechanism 256 are often subjected to high noise factors (e.g., from the motor generating bursts of flow in the system). In some implementations, the system 202 is provided at an upper fitment region of the pump (e.g., upper tubing fitment receptacle 254) above the pumping mechanism 256, and the flow stop would not be part of the flow sensor. In such implementations, the administration set would have two separate fitments: one containing (a standalone) flow sensor and associated control circuitry, and the other (lower) fitment having the flow stop clamp. Placing the flow sensor and control circuitry near the upper tubing fitment receptacle 254 allows the flow rate to be measured at a region of the pump that has lower noise factors, yielding more accurate measurements. The lower noise factors also allow a dynamic range of the flow rate measurements to be improved. In some implementations, the flow sensor 406 measures a dynamic range of flow rates between 0.1 ml/hour to 999 ml/hour.

Figure 3:
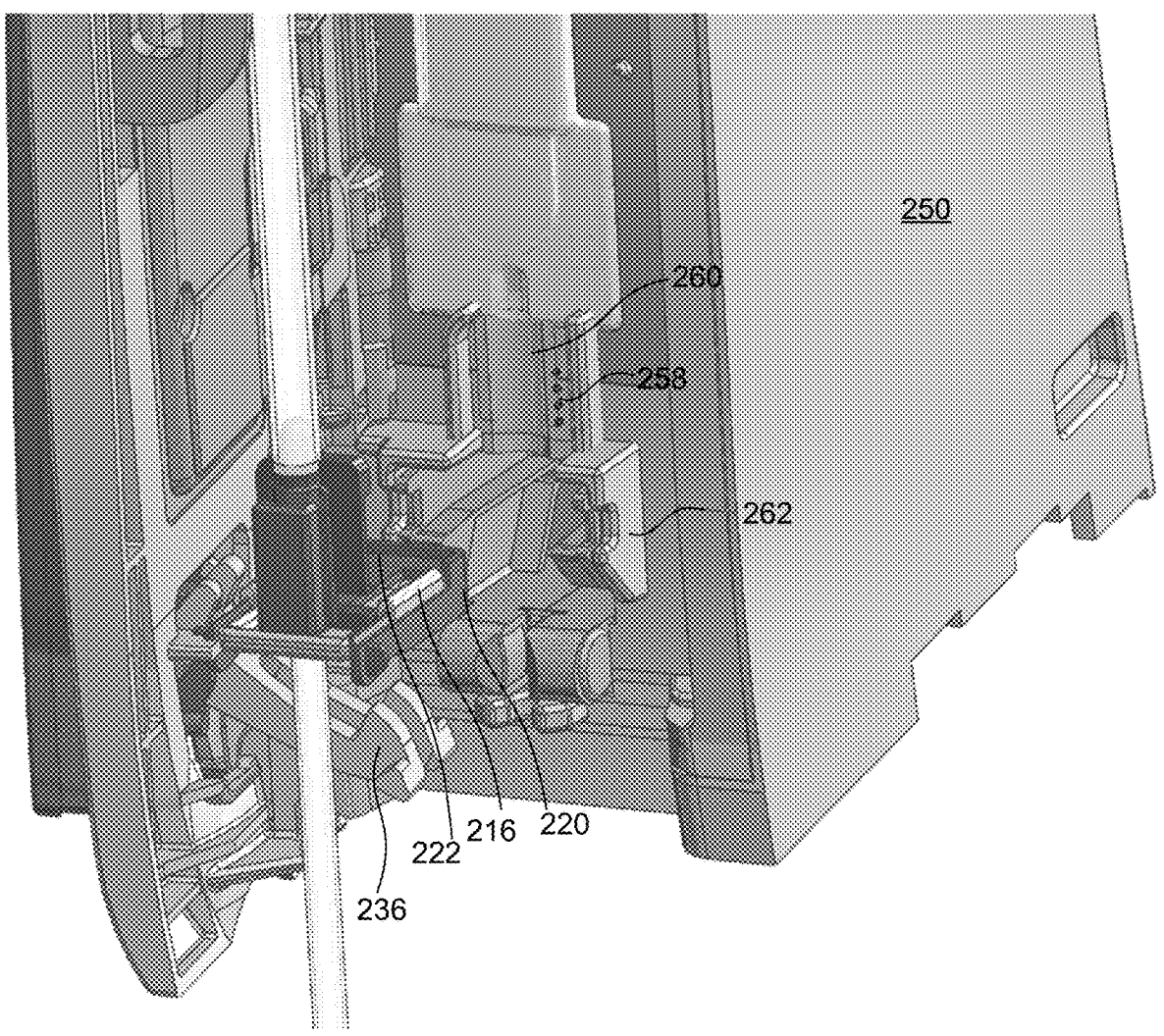
FIG. 3 depicts an enlarge view of an integrated administration set and an infusion pump, according to aspects of the subject technology.

Even though FIGS. 2 and 3 show insertion of the integrated flow stop system 202 at the lower region of the pump 250, the administration set according to aspects of the subject technology can be inserted at other regions of the pump 250.

In some implementations, instead of the entire integrated flow stop system 202 being positioned (e.g., inserted) at the upper tubing fitment receptacle 254, only the electronics contained in the housing 450 (e.g., the electronic flow sensor 406, the control circuitry, the wireless communication module, the inductive coupling elements) are inserted (e.g., while encased in a housing) at the top. In such implementations, the tubing fitment 222 and the flow stop 210 are still inserted below the pumping mechanism 256, similar to the configuration shown in FIG. 2. In such a configuration, the components included in the upper tubing fitment may be conductive coupled to the flow stop 210. In this way, resources such as power and data may be conducted via the flow stop 210 to the components included in the upper tubing fitment. A conductive path may be formed on or within a wall of the administration set or the conductive path may be wireless. In other words, the flow sensor may be part of the upper fitment and the electric power or communication may be part of the flow stop in lower fitment.

FIG. 3 depicts an enlarged view of an integrated administration set and an infusion pump, according to aspects of the subject technology. In some implementations, a portion of the pump 250 receives the integrated administration set 200. The molded feature 260 has a shape complementary to the housing 450 of the integrated flow stop system 202. The plurality of vertically arranged conductive connections 258 is embedded in the pump housing, and interfaces with the conductive connections in the integrated flow stop system 202 (shown more clearly in FIGS. 4A-4C). FIG. 3 depicts more clearly how the receiving portion 262 is to engage the pump side alignment region 220 of the tube fitment 222.

FIG. 4A depicts a first perspective view of an integrated flow stop system, according to aspects of the subject technology. As shown in a close up view of the integrated flow stop system 202, the integrated flow stop system 202 includes a tubing fitment 222, a housing 450, and a flow stop 210. The tubing fitment 222 includes a protrusion 228 that is configured to receive a tubing 212. The integrated flow stop system 202 includes a flow stop 210. The flow stop 210 includes a slider portion 216. The flow stop 210 is movably mounted to the tubing fitment 222, and positioned below the tubing fitment 222. The slider portion 216 of the flow stop 210 is able to slide along a channel defined in the tubing fitment 222.

The flow stop 210 is a clamping device, or safety clamp, that prevents inadvertent free-flow of fluids in the tubing 212 when the administration set 200 is removed from infusion device. The slider portion 216 slides along a direction 410 annotated by a double arrow. When the slider portion 216 slides closer to a pump side alignment region 220 of the fitment 222, the flow stop 210 is in an open position, which allows a fluid to flow through the tubing 212 from a top portion of the integrated flow stop system 202 to a tubing 214 connected to a lower portion of the integrated flow stop system 202. When the slider portion 216 slides toward a tubing side region 230 of the fitment 222, a rounded region 224 of a tear-shaped opening 218 moves away from the tubing 214, so that the narrower region 226 of the flow step 210 engages the tubing 214 and mechanically constricts (e.g., pinches or clamps) the tubing 214, occluding the flow of fluid in the tubing 214. In this closed position, the edge portion 230 of the flow stop 210 extends beyond (e.g., sticks out) the tubing side region 230 of the fitment 222, along the direction 410.

When the administration set 200 is properly loaded into (e.g., engaged with) and received by the pump 250, the flow stop 210 in the administration set 200 is maintained in the open state where fluids can flow through the tubing 214. When the infusion process is interrupted (e.g., by opening the door 252 of the pump 250), the flow stop 210 shifts into the closed position, to prevent accidental discharge of the fluid while the infusion process is interrupted. For example, the door 252 may include a latching element that secures the door in place against the pump 250. When the handle attached to the front face of the door 252 is lifted, this lifting action may release the latching element. In doing so, the change in position of the latching element may change the position of the flow stop 210 to the closed position. In some implementations, the opening of the door applies the force necessary to shift the flow stop 210 to the closed position. For example, a flange 236 may engage below the flow stop 210. When the door 252 is opened, the flange will be pulled away from the pump 250 and flow stop 210. As the flange leaves the pump 250, it may slide the flow stop 210 into the closed position.

Conventional administrative sets typically rely on flow sensors that external or that are built into the pump. Having a flow sensor incorporated into a flow stop allows for higher sensitivity in measuring different flow rates. The flow stop 210 may include a door-facing housing 234. The door-facing housing 234 may additionally or alternatively include conductive connectors to couple with connectors affixed on the door 252. The door-facing housing 234 may include electronic components to implement one or more of the features described, such as sensors, a microprocessor, memory, power, antenna, valve or valve controller (e.g., piezoelectric or electromagnetic controller), and/or fiber optics.

In some implementations, the flow stop is on the downstream section of the pump so that the flow going to the patient is more accurately controlled for flow continuity. Monitoring the flow on the upstream side measures the intake flow rate. In some implementations, the intake is filled very rapidly to allow flow continuity downstream. It may thus be desirable to monitor the flow on the downstream section of the pump. Assuming that there are no leaks or restrictions from the pump down to the needle (e.g., site of fluid entry into the patient), the location of flow monitoring should not matter. Placing the flow sensor near, or in the pump reduces the lengths of conductive (e.g., electrical) leads.

FIG. 4B depicts a second perspective view of an integrated flow stop system, according to aspects of the subject technology. As shown, a flow stop 210 is in the open position. In the open position, the rounded region 224 of the tear-shaped opening 218 does not mechanically obstruct a flow of fluid in the tubing 214. In the open position, an edge 232 of the flow stop 210 does not protrude beyond the tubing side region 230 of the tubing fitment 222.

FIG. 4C depicts a third perspective view of an integrated flow stop system, according to aspects of the subject technology. A view of the integrated flow stop system 202 from the pump side shows a number of conductive connections 402-a to 402-e in a recessed portion 404 of the housing 450 of an upper part of the integrated flow stop system 202. The fitment 222 forms the lower part of the system 202. The recessed portion 404 allows easier alignment of the conductive connections to a corresponding receiving portion of conductive connections on the pump 250. As shown in FIG. 4C, the flow stop system 202 includes five conductive connections whereas the pump interface includes four (see FIG. 3, element 258). The conductive connections may differ between the flow stop system 202 shown in FIG. 4C and the pump. This allows the flow stop system 202 to interface with a variety of different pumps and, as resources are available, increase the functionality provided thereby. In some instances, the flow stop system 202 may be inoperable without sufficient connectivity with the pump. In such instances, the flow stop system 202 may include a valve that remains closed to prevent fluid from infusing through the administration set. In such instances, the pump may receive a message from the flow stop system 202 disabling infusions through the pump until the administration set is changed.

The housing 450 of the integrated flow stop system 202 includes one or more flow sensors. In some implementations, at least a portion of a flow sensor may be in contact with the fluid. In such implementations, the flow sensor may include a metering element in the fluid path that can move based on the rate of fluid moving along the fluid path. In some implementations, the inline pressure (or differential pressure) of fluid along the fluid path or constricted fluid path may be measured to determine the flow rate.

In some implementations, the fluid may not be in contact with the flow sensors. In some implementations, the flow sensor may include two components, one within the housing 450 and one within the door-facing housing 234. An emission from one component may be read by the second component. A comparison between the emitted signal and the received signal may provide an indication of flow rate. In some implementations, the flow sensor may include an acoustic sensor. The acoustic sensor may detect the noise within the fluid line as the fluid is flowing past the sensor. The detected noise may be used to identify the flow rate. In some implementations, the acoustic sensor includes an ultra-sonic method of flow sensing.

In some implementations, the flow sensors operate based on calorimetric principles. For example, a static heating element and two temperature sensors are placed in the fluid path, and the flow rate is measured based on changes in the temperature profile of the fluid. Such flow sensors may be CMOS based. In some implementations, the flow sensors operate based on time-of-flight principles. Unlike static heaters, the heater based on time-of-flight principles is modulated and receivers both upstream and downstream of the heater receive the modulated signal. Based on the time of arrival of the modulated signal, the flow rate is deter-mined. In some implementations, such flow sensors may be packaged as MEMS.

In some implementations, electrical energy for powering the flow sensors are transmitted from the pump through the conductive connections 402-*a* to the flow sensors. The flow sensors send data back to the pump 250 through one of the conductive connections. In some implementations, the con-ductive connections 402-*a* and 402-*e* include pogo-pin type connectors. In some implementations, the conductive con-nections 402-*a* and 402-*e* include elastomeric plastic con-ductor material. In some implementations, the conductive connections 402-*a* and 402-*e* form a conductive connection with an inductive power source housed within the pump. The inductive power source includes inductive coupling components configured to transfer power wirelessly from the pump to the electronic flow sensor. In such cases, the conductive connections need not be formed on an exposed surface of the housing 450 in the upper part of the integrated flow stop system 202.

In some implementations, the integrated flow stop system 202 includes wireless communication circuitry, allowing the administration set 200 to form a wireless association with the pump and/or a server system. In some implementations, the wireless association is formed automatically, without specific user input. Such wireless connectivity allows a server system to track locations of particular administration sets, and also allows the server system to receive informa-tion about flow rates of therapeutic treatments provided by different administration sets.

The housing 450 in the upper part of the system 202 may also contain various circuitry that allows the pump to identify a particular administration set. Non-volatile memory in the circuit can store information regarding a manufacture date of the administration set 200, allowing the pump to ascertain if the administration set 200 has exceeded a particular shelf-life. In some implementations, to ensure patient safety, the pump would not proceed with an infusion process when the pump reads from the non-volatile memory of the integrated flow stop system 202 that administration set 200 has exceeded its shelf-life. In some implementations, the administration set has degraded accuracy towards its end of life, and the pump would be able to obtain life-time information from the non-volatile memory of the adminis-tration set 200. The integrated flow stop system 202 thus provides a smart sensor for the pump 250. The pump is also able to record the usage time clocked on a particular administration set. In some implementations, when a patient is moved between different zones in a hospital (e.g., from the intensive care unit, to a general ward), the same adminis-trative set is used/associated with different pumps, and the circuitry on the integrated flow stop system 202 provides information to the hospital system regarding a total duration of the therapeutic treatment.

The circuitry contained within the housing 450 in the upper part of the integrated flow stop system 202 also includes closed loop flow control circuitry. In some imple-mentations, the closed loop flow control circuit directly receives real-time data recorded by the flow sensors (or other sensors included in the flow stop such as a temperature sensor, a light sensor, a camera, a gyro sensor or acceler-ometer to identify if the set has been properly inserted by the user, a near-field communication (NFC) sensor for power-ing, communication and/or authentication of an authorized administration set, a Bluetooth Low Energy (BLE) beacon for asset tracking and for identifying active infusions and administration sets) and provides control signals to the pump 250 to alter a flow rate of the pump to achieve a desired therapeutic fluid flow rate profile for the infusion. In some implementations, the flow sensors include electrical capaci-tance sensors that measure flow based on the changes in dielectric caused by fluid flow. In some implementations, it may be desirable to provide measurements to the pump and allow the pump to assess and apply adjustments to achieve the target pumping conditions.

Having the flow sensors provide real-time measured data to the close-loop flow control circuit contained within the housing 450 of the integrated flow stop system 202 mini-mizes or, in some cases, eliminates the need to transfer raw flow rate data to the pump and reducing latency between detecting the flow rate and the pump receiving, computing and adjusting a flow rate. In some implementations, the housing 450 of the integrated flow stop system 202 may include newer control circuitry and/or firmware, allowing even an older version of the pump to provide enhanced flow control or other fluid characteristic sensing based on the control circuitry in the administration set, without having the need to retrofit or modify the pump or to add and coordinate additional sensors. In some implementations, additional circuitry provides the capability of updating the flow stop firmware over the air so that algorithms can be enhanced to improve flow sensitivity without needing to reconfigure a pump that is already deployed in the field. In some imple-mentations, older pumps that have mating connections can connect with a flow stop having corresponding conductive connections (e.g., electrically conductive connections and data conductive elements).

In some implementations, the measured flow rate or other fluid characteristic data is stored on the administration set. In some implementations, the measured flow rate or other fluid characteristic data is stored in the system (e.g., on the pump, or on a server system (e.g., in a hospital system)).

The pump includes flow rate values for different fluid types. By measuring the flow rate and controlling the flow rate in closed loop, right on the administration set, higher accuracy is achieved. The higher accuracy permits better predictions of the amount of therapeutic fluid that is going to be infused to the patient. The system 250 detects risks of unregulated flows (e.g., over-infusion, under-infusion) and preemptively corrects for any infusion rate errors.

Figure 5A:
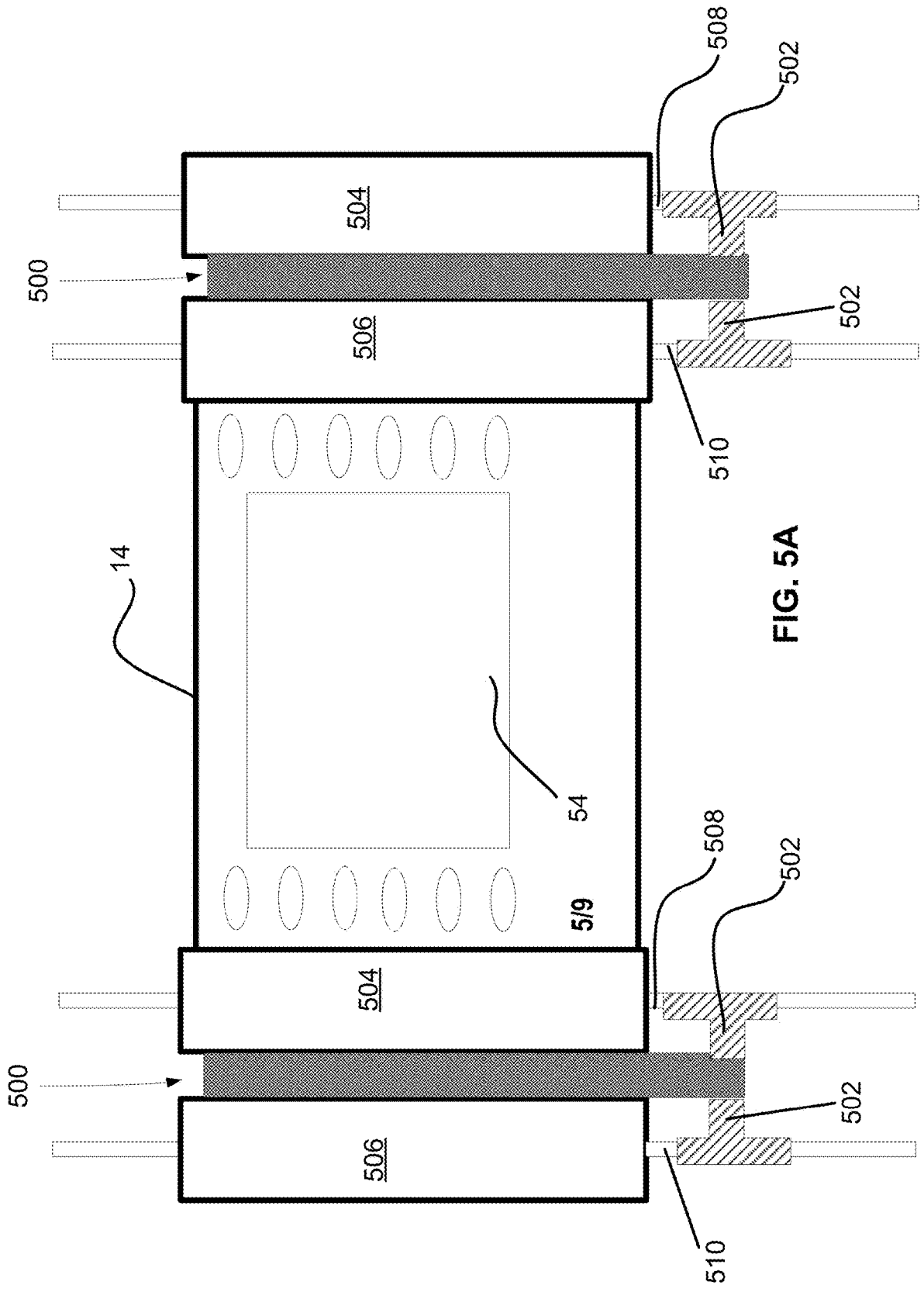
FIG. 5A depicts an example sensor system that is retrofitted to an infusion device, according to aspects of the subject technology.
Figure 5D:
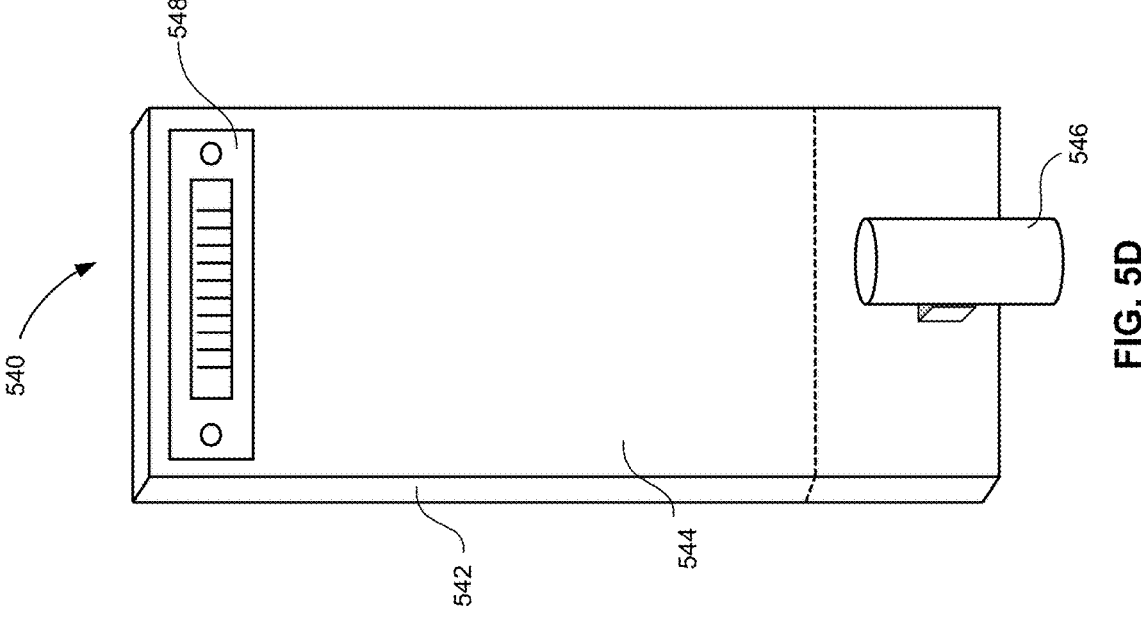
FIG. 5D depicts an example sensor system, according to aspects of the subject technology.
Figure 5B:
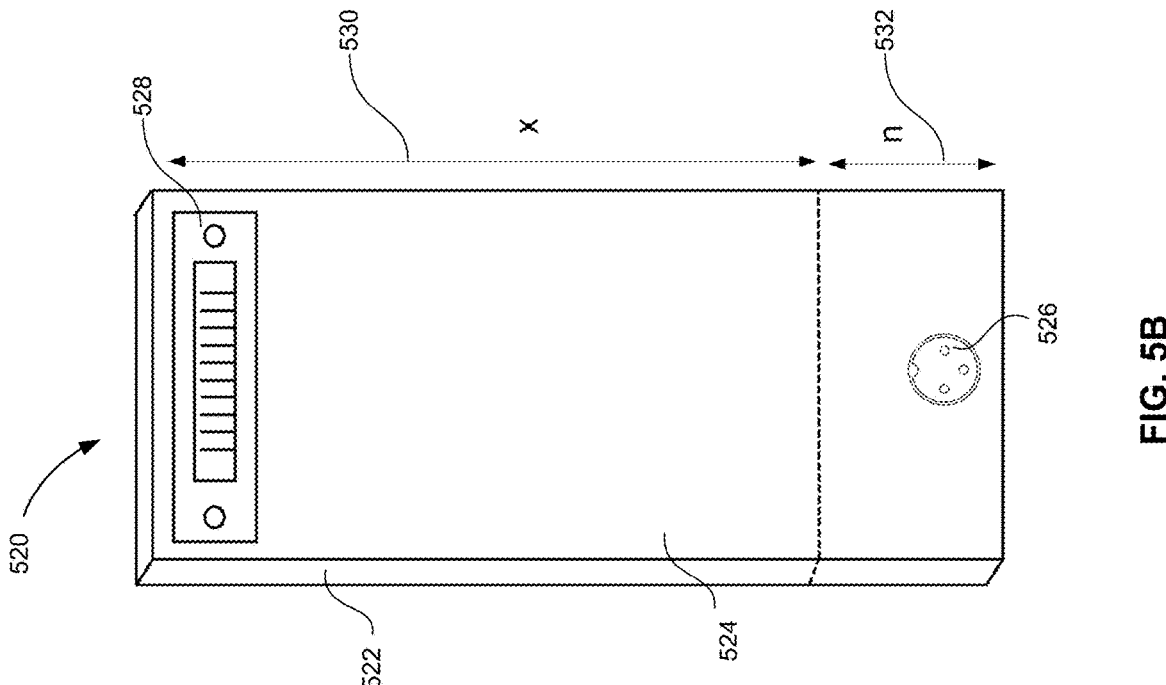
FIG. 5B depicts an example sensor system that includes a device having a port for receiving a flow sensor, according to aspects of the subject technology.
Figure 5C:
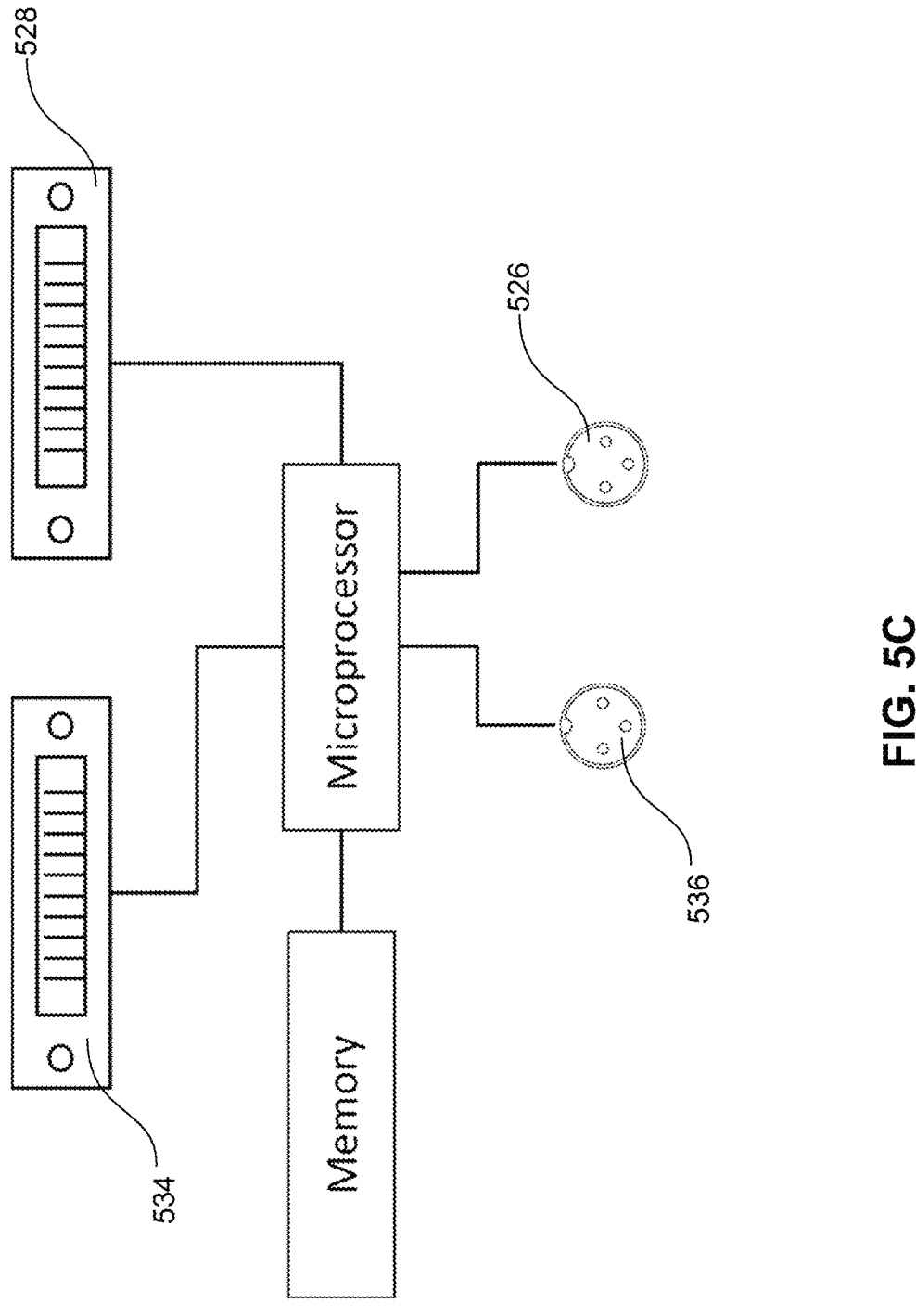
FIG. 5C depicts an example sensor system configured to couple more than one sensors and more than one pump modules, according to aspects of the subject technology.
Figure 5E:
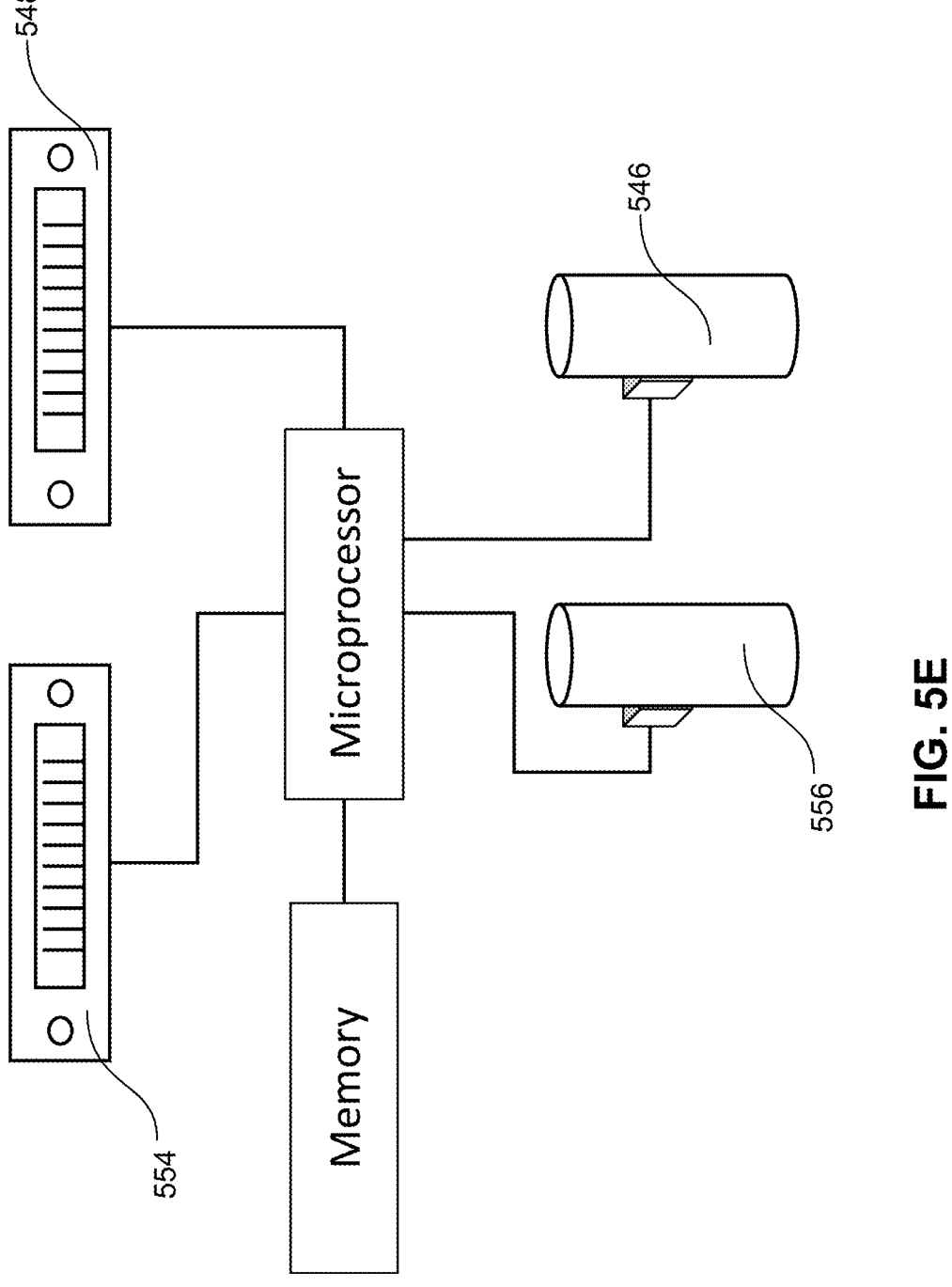
FIG. 5E depicts an example sensor system configured to couple more than one pump modules, according to aspects of the subject technology.

FIG. 5A depicts an example sensor system that is retro-fitted to an infusion device, according to aspects of the subject technology. Instead of the integrated flow stop system 202 establishing electrical or data connections to a control module 14 (e.g., the pump 250), a sensor wedge 500 has one or more sensor plugins 502 to couple one or more distinct administration sets (e.g., 508, 510) infusing one or more fluids to a patient via an integrated flow stop system (similar to the flow stop system 202 described in FIGS. 2-4D). In some implementations, various flow features can be integrated into the one or more sensor plugins 502. In some implementations, sensor features are plugged into the wedge (as shown in FIG. 5B and FIG. 5C) or are included in (e.g., affixed to) the wedge (as shown in FIGS. 5D and 5E). When the sensor features are included in the sensor 500, the administration sets (e.g., 508, 510) can be loaded into the sensor plugin 502 for non-contact sensing (e.g., through the tubing without direct contact with the fluid).

In some implementations, modules 504 and 506 may include different pumps, such as a large volume pump (LVP), a syringe pump, or an end-tidal CO2 monitor (EtCO2). In some implementations, the sensor plugins may be clamped externally to the administration set rather than couple with or be integrated into the administration sets. In this way, the sensor plugins may be reused for multiple infusions. In some implementations, the sensor plugins are integrated into the administration set and include one or more conductive coupling elements to connect with the sensor wedge.

The control module 14 may include a user interface device 54. The sensor wedge 500 can be retrofitted to pumps to provide sensing capabilities via the IUI connector 266 (shown in FIG. 2). Data and power may be transferred via the IUI connector 266. The sensor wedge may include similar circuitry as the flow stop such as a microprocessor, memory, power storage, antenna, sensors, etc. The sensor plugins may provide measurements to the sensor wedge 500. As discussed, the sensor wedge may process the measurements and provide control messages to adjust the pump. In some implementations, the sensor wedge may forward sensor readings to the pump and allow the pump to assess the proper controls. In some implementations, the sensor wedge allows the flow sensor and the control circuitry to be located on the top tube fitment, instead of the lower fitment.

FIG. 5B depicts an example sensor system that includes a device having a port for receiving a flow sensor, according to aspects of the subject technology. FIG. 5B shows a view of one side of a wedge sensor 520. The wedge sensor 520 has a housing 522. In some implementations, the housing 522 has a first main surface 524 and a second main surface (not shown in FIG. 5B) parallel to the first main surface 524. A processor of the wedge sensor 520 is located inside the housing 522. Storage memory is also located inside housing 522.

The wedge sensor 520 includes a connection element 528 mounted on the first surface 524 of the housing 522. In some implementations, the connection element 528 is an inter-unit interface connector configured to mate with the IUI connector on a pump module or a patient care unit (PCU). The connection element 528 includes a data conductive element to transfer data from the wedge sensor 520 to the pump module or the PCU. The connection element 528 also includes an electrically conductive element to transfer power. In some implementations, the connection element 528 receives power from the infusion device, and the data is transferred between the sensor system and the infusion device. In some implementations, the connection element 528 includes a mounting element to attach to a corresponding interface connector of the infusion device. In some implementations, the infusion device has a predetermined length, and the first surface 524 of the housing 522 has a length exceeding the predetermined length such that the first electronic flow sensor can extend from the first surface 524 under or above the infusion device.

In some implementations, the inter-unit interface connector 528 includes a mounting element to attach to a corresponding interface connector of a first infusion device, and the second inter-unit interface connector 534 includes a second mounting element to attach to a corresponding interface connector of a second infusion device. In some implementation, power is received from the first infusion device, and data is transferred between the sensor system and the first infusion device. In some implementation, power received by the second inter-unit interface connector 534 includes at least a portion of the power received by inter-unit interface connector 528, and is transmitted to the second infusion device. Data received by the second inter-unit interface connector 534 includes at least a portion of the data transferred between the sensor system and the first infusion device, and is transferred between the sensor system and the second infusion device.

The wedge sensor 520 includes, on the first main surface 524, an electronic flow sensor port 526 for receiving a flow sensor. In some implementations, the port 522 includes three pins as shown in FIG. 5B. In some implementations, there may be more or fewer pins, depending on the power and data capabilities of the flow sensor. The port 526 is configured to receive flow information from a first electronic flow sensor of a first fluid line (e.g., from an administration set) that is coupled to it. The data conductive element, the electrically conductive element, and the electronic flow sensor port are coupled with the processor.

A second connection element 534 (shown in FIG. 5C) is mounted on the second surface of the housing 522. In some implementations, the second connection element is similar to the connection element that is mounted on the first main surface 524: it is configured to mate with the IUI connector on the pump module or PCU; it includes a second data conductive element to transfer second data from the wedge sensor 520 to the pump module or the PCU; and it includes a second electrically conductive element to transfer power.

A second electronic flow sensor port 536 (shown in FIG. 5C) is also mounted on the second main surface. In some implementations, the second electronic flow sensor port is similar to the electronic flow sensor port 526 that is mounted on the first main surface 524: it is configured to receive flow information from a second electronic flow sensor of a second fluid line (e.g., from an administration set) that is coupled to it. The second data conductive element, the second electrically conductive element, and the second electronic flow sensor port are also coupled with the processor.

In some implementations, a first portion 530 of the housing 522 has a height x that corresponds to height of the pump module. A second portion 532 of the housing 522 includes the port 526, and has a height n. In some implementations, a sum of the height of the first portion 530 and a height of the second portion 532 exceeds the height of the pump module, providing clearance for the sensors.

FIG. 5C depicts an example sensor system configured to couple more than one sensors and more than one pump modules, according to aspects of the subject technology. FIG. 5C shows the coupling between the microprocessor in the wedge sensor 520 and various connectors and ports. In some implementations, the first IUI connector 528 and the first electronic flow sensor port 526, both of which are mounted to a first main surface 524 of the housing 522 are coupled to the microprocessor. The microprocessor in the wedge sensor 520 is also coupled to the second IUI connector 534 and the second electronic flow sensor port 536, both of which are mounted to the second main surface of the housing 522. Storage memory or other memory is also coupled to the microprocessor. In other words, the wedge sensor 520 includes two sensor ports (one on each side of the wedge sensor 520) and is configured to be coupled to two PCUs (one on each side of the wedge).

FIG. 5D depicts an example sensor system, according to aspects of the subject technology. FIG. 5D shows a view of one side of a wedge sensor 540. The wedge sensor 540 has a housing 542. In some implementations, the housing 542 has a first main surface 544 and a second main surface (not shown in FIG. 5D) parallel to the first main surface 544. A processor of the wedge sensor 540 is located inside the housing 542. Storage memory is also located inside housing 542.

The wedge sensor 540 includes a connection element 548 mounted on the first surface 544 of the housing 542. In some implementations, the connection element 548 is an IUI connector configured to mate with the IUI connector on an infusion device (e.g., the pump module or PCU). The connection element 548 includes a data conductive element to transfer data from the wedge sensor 540 to the pump module or the PCU. The connection element 548 also includes an electrically conductive element to transfer power. In some implementations, the connection element 548 receives power from the infusion device, and the data is transferred between the sensor system and the infusion device. In some implementations, the connection element 548 includes a mounting element to attach to a corresponding interface connector of the infusion device. In some implementations, the infusion device has a predetermined length, and the first surface 544 of the housing 542 has a length exceeding the predetermined length such that the first electronic flow sensor can extend from the first surface 544 under or above the infusion device.

In some implementations, the inter-unit interface connector 548 includes a mounting element to attach to a corresponding interface connector of a first infusion device, and the second inter-unit interface connector 554 includes a second mounting element to attach to a corresponding interface connector of a second infusion device. In some implementation, power is received from the first infusion device, and data is transferred between the sensor system and the first infusion device. In some implementation, power received by the second inter-unit interface connector 554 includes at least a portion of the power received by inter-unit interface connector 548, and is transmitted to the second infusion device. Data received by the second inter-unit interface connector 554 includes at least a portion of the data transferred between the sensor system and the first infusion device, and is transferred between the sensor system and the second infusion device.

An electronic flow sensor 546 affixed to the first main surface 544 is configured to measure flow information for a first fluid line coupled to it. The data conductive element, the electrically conductive element, and the first electronic flow sensor are coupled with the processor.

A second connection element 554 (shown in FIG. 5E) is mounted on the second surface of the housing 552. In some implementations, the second connection element is similar to the connection element that is mounted on the first main surface 554: it is configured to mate with the IUI connector on the pump module or PCU; it includes a second data conductive element to transfer second data from the wedge sensor 550 to the pump module or the PCU; and it includes a second electrically conductive element to transfer power. A second electronic flow sensor 556 (shown in FIG. 5E) affixed to the second surface is configured to measure flow information for a second fluid line coupled to it. The second data conductive element, the second electrically conductive element, and the second electronic flow sensor port are also coupled with the processor.

FIG. 5E depicts an example sensor system configured to couple more than one pump modules, according to aspects of the subject technology. FIG. 5E shows the coupling between the microprocessor in the wedge sensor 540 and various connectors and ports. In some implementations, the first IUI connector 548 and the first electronic flow sensor 546, both of which are mounted to a first main surface 544 of the housing 542 are coupled to the microprocessor. The microprocessor in the wedge sensor 540 is also coupled to the second IUI connector 554 (mounted to the second main surface of the housing 542) and the second electronic flow sensor 556. Storage memory or other memory is also coupled to the microprocessor. In other words, the wedge sensor 540 includes two sensors (one on each side of the wedge sensor 540) and is configured to be coupled to two PCUs (one on each side of the wedge).

In one aspect, an integrated intravenous (IV) administration set includes a flow stop having a tubing fitment and a housing, the flow stop configured, in a first position, to prevent a flow of a fluid through a tubing, and in a second position, to permit the flow of the fluid through the tubing, the tubing fitment comprising a protrusion configured to receive a tubing. The IV administration set also includes an electronic flow sensor disposed within the housing, the electronic flow sensor configured to measure the flow of the fluid in the tubing, and one or more conductive connections configured within the housing and configured to provide electrical power to the electronic flow sensor. The flow stop is shaped to be loaded and engaged to a receptacle of an infusion device, and shaped to cause, when loaded and engaged, the one or more conductive connections to engage with a corresponding conductive connection provided by the infusion device to activate the electronic flow sensor based on a power flow from the infusion device.

In some implementations, the integrated intravenous (IV) administration set further includes control circuitry is configured to send a control signal to the infusion device to modify a flow rate generated by a pumping mechanism of the infusion device. In some implementations, the electronic flow sensor further includes a data communication component. The one or more conductive connections is arranged on an exterior of the housing, and the infusion device is configured with a corresponding one or more conductive connections so that during use of the integrated IV administration set: the one or more conductive connections is in electrical contact with the corresponding one or more conductive connections, and the electronic flow sensor is in electrical communication to transmit data using the data communication component to the infusion device.

In some implementations, the housing includes a recessed portion, and the one or more the conductive connections is vertically aligned within the recessed portion. In some implementations, the one or more conductive connections includes spring loaded pogo pin connectors. In some implementations, the one or more conductive connections includes an elastomeric plastic conductor material. In some implementations, the tubing fitment has a shape complementary to features molded into a housing of the infusion device so that the tubing fitment is configured to align the flow stop with respect to the infusion device when the integrated IV administration set is loaded and engaged to the infusion device.

In some implementations, the integrated IV administration set further includes a wireless communication module. In some implementations, the integrated IV administration set is configured to wirelessly upload data measured by the electronic flow sensor to a server system that monitors an operation of the infusion device.

In some implementations, the integrated IV administration set is configured to wirelessly transfer data measured by the electronic flow sensor to the infusion device.

In some implementations, the one or more conductive connections include inductive coupling components configured for wireless power transfer from the infusion device to the electronic flow sensor.

In some implementations, the integrated IV administration set further includes non-volatile memory components storing identification information of the integrated IV administration set. In some implementations, the non-volatile memory components store information about a manufacture date of the integrated IV administration set, and the infusion device is configured to check the identification information and the manufacture date of the integrated IV administration set prior to starting an infusion process.

In some implementations, the non-volatile memory components store information that is transmitted to the infusion device, the information indicating how long the integrated IV administration set has been in used.

In some implementations, the flow stop includes a slider component mounted to and positioned orthogonal to the tubing fitment. The slider component is configured to slide relative to the tubing fitment and engage a tubing connected to the tubing fitment to prevent a flow of fluid in the tubing when the IV administration set is removed from the infusion device and to allow the flow of fluid in the tubing when the IV administration set is loaded and engaged to the infusion device.

In some implementations, the tubing fitment and the housing are configured to be received in a top portion of the infusion device, the top portion of the infusion device being above a pumping mechanism of the infusion device, and the flow stop is configured to be received in a bottom portion of the infusion device, the bottom portion of the infusion device being below the pumping mechanism of the infusion device.

In some implementations, the flow sensor is configured to send a control signal to the infusion device after the integrated IV administration set has been in use for a predetermined period of time.

In some implementations, the IV administration set further includes a processor configured to determine a duration of time the integrated IV administration set has been in use based on a length of time the integrated IV administration set receives electrical power from the infusion device through the one or more conductive connections.

In another aspect, a sensor system includes a first plurality of conductive connections; a data port to receive data recorded by an electronic flow sensor of an integrated intravenous (IV) administration set, wherein the integrated IV administration set includes a second plurality of conductive connections configured to interface with the first plurality of conductive connections when the integrated IV administration set engages with the sensor system; and the sensor system is configured to provide control signals to an infusion device based on the data recorded by the electronic flow sensor to maintain a fluid flowing through the integrated IV administration set at a desired flow rate.

Many of the above-described features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 6:
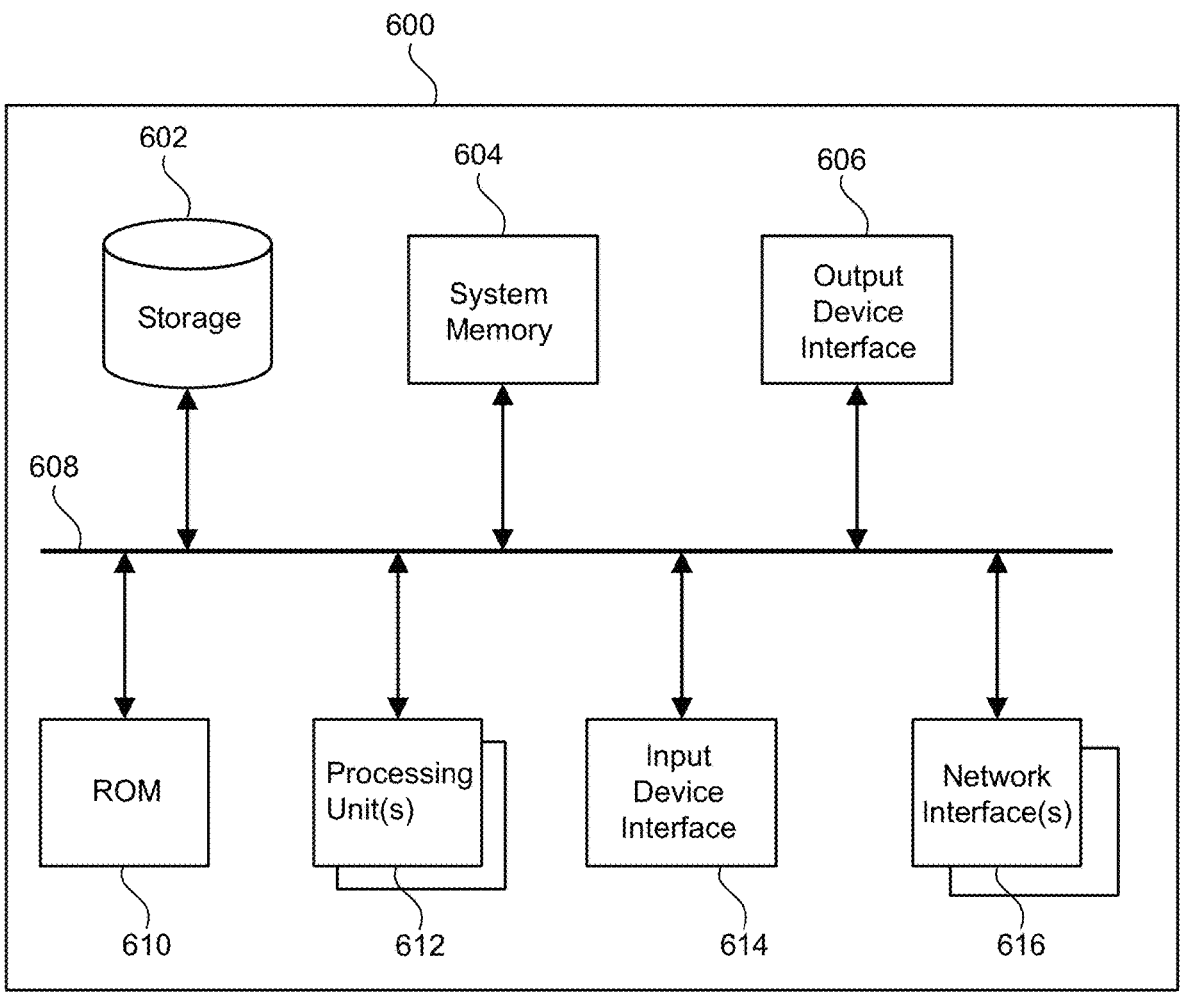
FIG. 6 is a conceptual diagram illustrating an example system for sensing and controlling liquid flows in infusion processes, according to aspects of the subject technology.

FIG. 6 is a conceptual diagram illustrating an example electronic system 600 for sensing and controlling liquid flows in infusion processes, according to aspects of the subject technology. Electronic system 600 may be a computing device for execution of software associated with one or more portions or steps of process 600, or components and processes provided by FIGS. 1-6, including but not limited to information system server 30, or computing hardware within patient care device 12. Electronic system 600 may be representative, in combination with the disclosure regarding FIGS. 1-6. In this regard, electronic system 600 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 600 may include various types of computer readable media and interfaces for various other types of computer readable media. In the depicted example, electronic system 600 includes a bus 608, processing unit(s) 612, a system memory 604, a read-only memory (ROM) 610, a permanent storage device 602, an input device interface 614, an output device interface 606, and one or more network interfaces 616. In some implementations, electronic system 600 may include or be integrated with other computing devices or circuitry for operation of the various components and processes previously described.

Bus 608 collectively represents all system, peripheral, and chipset buses that communicatively connect the numerous internal devices of electronic system 600. For instance, bus 608 communicatively connects processing unit(s) 612 with ROM 610, system memory 604, and permanent storage device 602.

From these various memory units, processing unit(s) 612 retrieves instructions to execute and data to process in order to execute the processes of the subject disclosure. The processing unit(s) can be a single processor or a multi-core processor in different implementations.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is off. Some implementations of the subject disclosure use a mass-storage device (such as a magnetic or optical disk and its corresponding disk drive) as permanent storage device 602.

Other implementations use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such a random access memory. System memory 604 stores some of the instructions and data that the processor needs at runtime. In some implementations, the processes of the subject disclosure are stored in system memory 604, permanent storage device 602, and/or ROM 610. From these various memory units, processing unit(s) 612 retrieves instructions to execute and data to process in order to execute the processes of some implementations.

Bus 608 also connects to input and output device interfaces 614 and 606. Input device interface 614 enables the user to communicate information and select commands to the electronic system. Input devices used with input device interface 614 include, e.g., alphanumeric keyboards and pointing devices (also called "cursor control devices"). Output device interfaces 606 enables, e.g., the display of images generated by the electronic system 600. Output devices used with output device interface 606 include, e.g., printers and display devices, such as cathode ray tubes (CRT) or liquid crystal displays (LCD). Some implementations include devices such as a touchscreen that functions as both input and output devices.

Also, as shown in FIG. 6, bus 608 also couples electronic system 600 to a network (not shown) through network interfaces 616. Network interfaces 616 may include, e.g., a wireless access point (e.g., Bluetooth or WiFi) or radio circuitry for connecting to a wireless access point. Network interfaces 616 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 600 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML, page) to a client device (e.g., for purposes of displaying data to and receiving user input from a user interacting with the client device). Data generated at the client device (e.g., a result of the user interaction) can be received from the client device at the server.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some implementations, include a signal utilized to transmit one or more representations of the information. While recited in the singular, it will be understood that a message may be composed, transmitted, stored, received, etc. in multiple parts.

In any implementation, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on web sites and the like.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term web site, as used herein, may include any aspect of a web site, including one or more web pages, one or more servers used to host or store web related content, etc. Accordingly, the term web site may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. A sensor system comprising:
a housing having a first surface and a second surface;
a processor disposed within the housing;
the first surface including:
a first inter-unit interface connector mounted on the first surface of the housing, the first inter-unit interface connector including a mounting element for attaching to a corresponding interface connector of an infusion device, a first data conductive element to transfer first data between the sensor system and the infusion device, and a first electrically conductive element to receive a first power from the infusion device, and
a first electronic flow sensor configured to measure flow information for a first fluid line coupled therewith, wherein the first data conductive element, the first electrically conductive element, and the first electronic flow sensor are coupled with the processor; and
the second surface including:
a second inter-unit interface connector mounted on the second surface of the housing, the second inter-unit interface connector including a second data conductive element to transfer second data and a second electrically conductive element to transfer second power, and
a second electronic flow sensor configured to measure flow information for a second fluid line coupled therewith, wherein the second data conductive element, the second electrically conductive element, and the second electronic flow sensor are coupled with the processor.

2. The sensor system of claim 1, wherein the infusion device has a predetermined length, and wherein the first surface of the housing has a length exceeding the predetermined length such that the first electronic flow sensor can extend from the first surface under or above the infusion device.

3. The sensor system of claim 1, wherein the second inter-unit interface connector includes a second mounting element to attach to a corresponding interface connector of a second infusion device.

4. The sensor system of claim 3, wherein the second power includes at least a portion of the first power, and wherein the second power is transmitted to the second infusion device, and wherein the second data includes at least a portion of the first data, and wherein the second data is transferred between the sensor system and the second infusion device.

5. The sensor system of claim 1, wherein the housing comprises:
a connection element comprising a data conductive element configured to transfer data from the sensor system to a first or second infusion pump module or to an infusion pump control unit.

6. The sensor system of claim 5, wherein the housing further comprises:
a non-volatile memory storing identification information of the sensor system.

7. The sensor system of claim 5, further comprising:
control circuitry configured to communicate with the first or second infusion pump module or to the infusion pump control unit, and to change an operational parameter of the first or second infusion pump module or to the infusion pump control unit in order to bring a flow rate measured by the first or second electronic flow sensor to as close as possible to a set flow rate.

8. The sensor system of claim 7, further comprising a wireless communication module, and wherein the processor is configured to wirelessly transfer data measured by the first or second electronic flow sensor to the first or second infusion pump module or to the infusion pump control unit.

9. A sensor system comprising:

a housing having a first surface and a second surface;

a processor;

the first surface of the housing comprising:

a first inter-unit interface connector comprising a mounting element to attach to a corresponding interface connector of an infusion device, a first data conductive element to transfer first data between the sensor system and the infusion device, and a first electrically conductive element to receive a first power from the infusion device, and a first electronic flow sensor port configured to receive flow information from a first electronic flow sensor coupled therewith for a first fluid line, wherein the first data conductive element, the first electrically conductive element, and the first electronic flow sensor port are coupled with the processor; and the second surface of the housing comprising:

a second inter-unit interface connector comprising a second data conductive element to transfer second data and a second electrically conductive element to transfer second power, and a second electronic flow sensor port configured to receive flow information from a second electronic flow sensor coupled therewith for a second fluid line, wherein the second data conductive element, the second electrically conductive element, and the second electronic flow sensor port are coupled with the processor.

10. The sensor system of claim 9, wherein the infusion device has a predetermined length, and wherein the first surface of the housing has a length exceeding the predetermined length such that the first electronic flow sensor port can extend from the first surface under or above the infusion device.

11. The sensor system of claim 9, wherein the second inter-unit interface connector includes a second mounting element to attach to a corresponding interface connector of a second infusion device.

12. The sensor system of claim 11, wherein the second power includes at least a portion of the first power, and wherein the second power is transmitted to the second infusion device, and wherein the second data includes at least a portion of the first data, and wherein the second data is transferred between the sensor system and the second infusion device.

13. The sensor system of claim 9, wherein the housing comprises:

a connection element configured to transfer data from the sensor system to a first or second infusion pump module or to an infusion pump control unit.

14. The sensor system of claim 13, wherein the housing further comprises:

a non-volatile memory storing identification information of the sensor system.

15. The sensor system of claim 13, further comprising:

control circuitry configured to communicate with the first or second infusion pump module or to the infusion pump control unit, and to change an operational parameter of the first or second infusion pump module or to the infusion pump control unit in order to bring a flow rate measured by the first or second electronic flow sensor and received by the first or second electronic flow sensor port to as close as possible to a set flow rate, and wherein the processor is configured to change an operational parameter after the sensor system has been in use for a predetermined period of time.

16. The sensor system of claim 15, further comprising a wireless communication module, and wherein the processor is configured to wirelessly transfer data measured by the first or second electronic flow sensor and received by the first or second electronic flow sensor port to the first or second infusion pump module or to the infusion pump control unit.

* * * * *